United States Patent [19]
Spangler et al.

[11] Patent Number: 4,551,624
[45] Date of Patent: Nov. 5, 1985

[54] ION MOBILITY SPECTROMETER SYSTEM WITH IMPROVED SPECIFICITY

[75] Inventors: Glenn E. Spangler, Lutherville; John N. Cox, Baltimore, both of Md.

[73] Assignee: Allied Corporation

[21] Appl. No.: 535,451

[22] Filed: Sep. 23, 1983

[51] Int. Cl.[4] .................... B01D 59/44; G01N 27/66
[52] U.S. Cl. .................... 250/287; 250/282; 422/98
[58] Field of Search ............ 250/287, 288, 282, 424, 250/281, 286, 283; 436/173; 422/98

[56] References Cited

U.S. PATENT DOCUMENTS

| | | | |
|---|---|---|---|
| 3,555,272 | 1/1971 | Munson | 250/41.9 |
| 3,621,239 | 11/1971 | Cohen | 250/287 |
| 3,920,987 | 11/1975 | Anbar et al. | 250/282 |
| 4,091,655 | 5/1978 | French et al. | 73/23 |
| 4,238,678 | 12/1980 | Castleman et al. | 250/381 |
| 4,259,573 | 3/1981 | Prober et al. | 250/287 |
| 4,311,669 | 1/1982 | Spangler | 422/98 |
| 4,374,090 | 2/1983 | McClure | 422/98 |
| 4,378,499 | 3/1983 | Spangler et al. | 250/287 |

OTHER PUBLICATIONS

Tannenbaum et al., Negative Chemical Ionization Mass Spectrometry-Chloride Attachment Spectra, Anal. Chem., vol. 47, No. 1, 1975.
Carr, Comparison of the Negative Reactant Ions Formed in the Plasma Chromatograph by Nitrogen, Air, Sulfur Hexafluoride as the Drift Gas with Air as the Carrier Gas, Anal. Chem., vol. 51, No. 6, May 1979.

Primary Examiner—Bruce C. Anderson
Assistant Examiner—Paul A. Guss
Attorney, Agent, or Firm—James R. Ignatowski; Russel C. Wells

[57] ABSTRACT

An ion mobility spectrometer system with improved specificity. The ion mobility spectrometer has a reaction chamber and a drift chamber, an ionization source disposed in the reaction chamber, an injection grid separating said reaction and drift chambers, a collector electrode disposed in the drift chamber and a sample input injecting the sample and carrier into the reaction chamber.

A source injects acetone and/or carbon tetrachloride as reagents into the carrier gas prior to entering the sample input. The acetone reactant forms a dimer ion in the positive ion spectrum which impedes the clustering of water and provides a narrow fixed peak in the ion spectrum which serves as a reference point in the ion spectrum for the algorithm used in the electronic control unit generating an output characteristic of the sample. The carbon tetrachloride reactant forms a $(H_2O)_nCl^-$ ion which provides a reference in the negative ion spectrum for the algorithm used in the electronic control unit. The acetone and carbon tetrachloride reactants both rendering the ion mobility spectrometer more specific for detection and identification.

34 Claims, 5 Drawing Figures

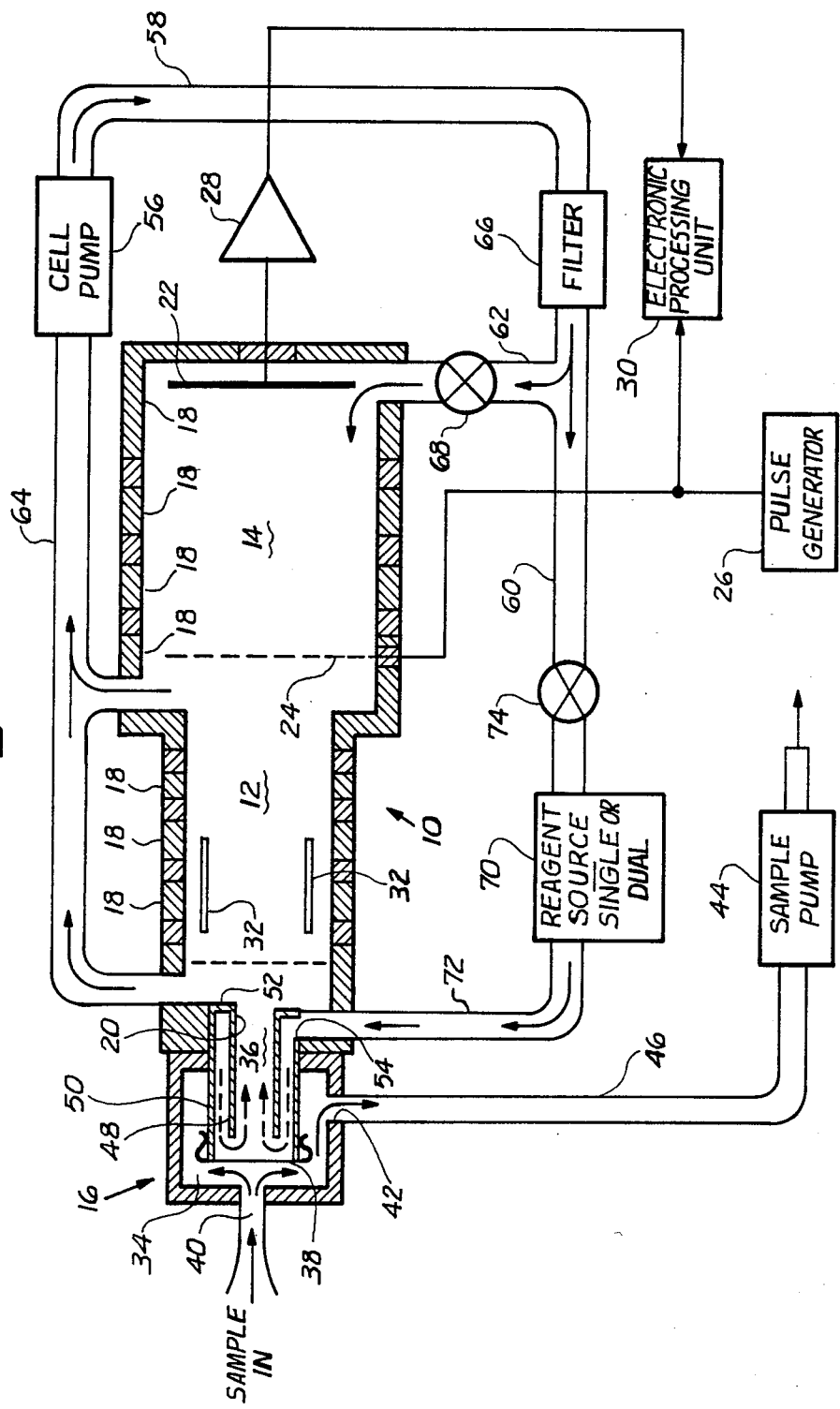

ION MOBILITY SPECTROMETER SYSTEM WITH IMPROVED SPECIFICITY

BACKGROUND OF THE INVENTION

1. Field of the Invention

The invention is related to the field of ion mobility spectrometers and in particular to an ion mobility spectrometer having means for continuously adding a chemical reagent vapor to the carrier gas in order to improve the selectivity of the spectrometer and eliminate the adverse affects of interferring vapors.

2. Prior Art

Ion mobility spectrometers are the primary instrument used in the field of plasma chromatography. The operation of the ion mobility spectrometer is similar to the operation of a time-of-flight mass spectrometer, the difference being that a time-of-flight spectrometer operates in a vacuum where the mean free path of the contained gases is may times the dimensions of the gas container whereas the ion mobility spectrometer operates at or near atmospheric pressure where the mean free path of the contained gas is smaller than the dimensions of the container. A typical ion mobility spectrometer, such as disclosed by Cohen et al, U.S. Pat. No. 3,621,240, comprises an ion/molecule reaction chamber, an ionization source associated with the ion reaction chamber, an ion drift chamber, an ion/molecule injector shutter or grid interposed between the ion reaction chamber and the ion drift chamber, and an ion collector. A carrier gas, normally purified air or nitrogen, is introduced into the ion mobility spectrometer to transport vapor from a sample material to be identified or detected. The carrier gas with the sample vapor are ionized by the ionization source in the ion/molecule reaction chamber. However, as is known in the art, the relative concentrations of the carrier gas and the sample vapor are such that the molecules of the carrier gas are more easily directly ionized by the ionization source than the molecules of the sample vapor. Since the mean free path for the ionized carrier molecules is many times smaller than the dimensions of the reaction chamber, there are multiple collisions between the ionized carrier molecules and the sample molecules. The tendency of these collisions is to transfer the ion charge from the ionized carrier molecules to the sample molecules. Therefore, the ionization of the sample gas is primarily by this secondary ionization process.

The charged molecules or ions are accelerated to a terminal velocity by an electrostatic field gradient within the ion/molecule reaction chamber causing them to travel towards the injection grid interfacing the ion drift chamber. Periodically, the bias on the injection grid is reduced to zero for a short period of time to permit a quantity (pulse) of ions to pass from the ion/molecule reaction chamber to the ion drift chamber. In the drift chamber, the passed ions are drawn, under the influence of an electrostatic drift field, to the ion collector where they are collected. The time of arrival of each ion species, both carrier gas and sample, at the ion collector is determined by the particular ion's mobility through the non-ionized gas filling the drift chamber. The heavier ions characteristically move slower through the drift chamber and arrive at the ion collector later than the lighter ions. It is thus possible to characterize the different ion species by monitoring the time between the introduction of the ions into the drift chamber at the injection grid and the arrival of the ions at the ion collector. An electrometer measures the quantity of ions collected by the ion collector.

As is known in the art, the sample vapor is injected into a carrier gas which transports the vapor molecules to the ion/molecule reaction chamber and exposes the vapor molecules to ion/molecule reactions with the ions generated in the ionized carrier gas. If it is desired to determine whether the atmosphere contains a certain constituent, usually a contaminant, the sample can simply be a sample of ambient air. However, certain constituents of atmospheric air, such as water, ammonia and nitrogen oxides, interfere with the proper performance of the ion mobility spectrometer. The effects of these components can be significantly attenuated through the use of a membrane inlet filter described in U.S. Pat. No. 4,311,669 issued Jan. 19, 1982. However, additional improvements in specificity are needed to allow ion mobility spectrometry to be used as a detector for specific sample materials in the presence of contaminants or other interferences.

One such improvement is described by Munson in U.S. Pat. No. 3,555,272. Munson discloses a method for generating sample ions in a mass spectrometer by mixing a reagent gas with the sample vapors. When the mixture is admitted into the ionization chamber of an ion source, the reagent gas is ionized first to form stable ions. The stable ions of the reagent gas then undergo ion/molecule reactions with the sample vapor to form ions characteristic of the sample vapor. The concentration of the sample in the ionized reagent gas is less than 1 percent. Similarly, Anbar et al in U.S. Pat. No. 3,920,987 disclose a method for detecting explosives in which a reagent gas comprising a mixture of sulfur hexafluoride ($SF_6$) and nitrogen ($N_2$) is first ionized in a separate chamber to form stable negative ions. The ionized reagent gas is then mixed with the sample vapor in an atmospheric pressure reaction chamber. In the atmospheric pressure reaction chamber electron exchange reactions occur to ionize the explosive constituent of the sample, before the ions are transmitted to a mass analyzer at reduced pressure for analysis. Sulfur hexafluoride ($SF_6$) was selected because it had a lower electron affinity than the explosive molecules in the sample but a higher electron affinity than the other constituents in the air which serves as the carrier for the explosive samples.

Finally, McClure in U.S. Pat. No. 4,374,090 discloses a method for detecting certain chemical agents in which a reagent gas of DMMP (dimethymethylphosphonate), TBA tributylamine, DIMP (diisopropylmethylphosphonate), DMSO (dimethylsulfoxide), di-N-butylamine and mixtures thereof are first ionized in the reaction chamber of an ionization detector as described in U.S. Pat. No. 3,835,328. The stable ions formed from the reagent gas then undergo ion/molecule reactions with the sample vapor to produce ions characteristic of the sample vapor which can be analyzed by the ionization detector.

Positive ion or proton transfer reactions are among the most important class of ion/molecule reactions used in ion mobility spectrometry. If M is the sample molecule and $RH^+$ is the reactant ion, ionization occurs in accordance with:

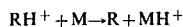

$$RH^+ + M \rightarrow R + MH^+$$

where $MH^+$ is the product ion. The tendency of the proton $H^+$, to transfer from the reactant ion $RH^+$ to the sample M is regulated by the relative proton affinities of R and M. The proton affinity of M must be greater than the proton affinity of R if the proton transfer reaction is to occur.

For the $(H_2O)_nH^+$ reactant ion conventionally used in ion mobility spectrometry, it has been shown that organophosphorous compounds, such as dimethylmethylphosphonate (DMMP), are ionized according to:

$$(H_2O)_nH^+ + DMMP \rightarrow (DMMP)H^+ + nH_2O$$

when n is small, i.e. n=4 or 5.

Additionally, cluster reactions can take place to yield:

$$M + MH^+ \rightleftharpoons M_2H^+$$

where $M_2H^+$ is the dimer ion.

As a result of the low proton affinity (173 Kcal/mole) of the $(H_2O)_nH^+$ reactant ion and its strong tendency to change cluster size with small variations in water concentration, two difficulties are encountered in its use as a reactant ion. First, the $(H_2O)_nH^+$ reactant ion loses charge to a large number of compounds, such as alcohols, ketones, aldehydes, esters, amines, pyridines, etc. which have proton affinities greater than itself and second, its cluster size changes with water concentration causing it to shift in drift time in the ion mobility spectrum. For a microprocessor controlled ion mobility spectrometer system, it is desirable to eliminate both of these problems in order to provide identification specificity.

Another important class of ion/molecule reactions used in ion mobility spectrometry is negative ion charge transfer or proton attraction reactions. If M is the sample molecule and $R^-$ is the reactant ion, ionization occurs in accordance with:

$$R^- + M \rightarrow R + M^- \quad \text{(charge transfer)}$$

$$R^- + M \rightarrow RH + (M-H)^- \quad \text{(proton abstraction)}$$

when
$M^-$ is the product ion for charge transfer
$H+$ is the proton
$(M-H)^-$ is the product ion for proton abstraction.

The tendency of an electron to transfer from the reactant ion, $R^-$, to the sample M is regulated by the relative electron affinities of R and M. The electron affinity of M must be greater than R if the charge transfer reaction is to take place. The tendency of a proton to transfer from the sample molecule M to the reactant ion $R^-$ is regulated by the acidity of M relative to R. The acidity of M must be greater than R if the proton abstraction is to take place.

For the $(H_2O)_nO_2^-$ or $(H_2O)_nCO_4^-$ reactant ions conventionally used in ion mobility spectrometry, it has been shown that nitroaromatic compounds, such as mononitrotoluene (MNT), are ionizated according to:

$$(H_2O)_nO_2^- + MNT \rightarrow MNT^- + nH_2O + O_2$$

or $$(H_2O)_nCO_4^- + MNT \rightarrow MNT^- + nH_2O + CO_2 + O_2$$

As a result of the low electron affinity (0.44 to 0.50 electron volts) of the $(H_2O)_nO_2^-$ and $(H_2O)_nCO_4^-$ reactant ion's and their strong tendency to change cluster size with small variations in water concentration, two difficulties are encountered in their use as reactant ions. First, they lose charge to a large number of compounds, such as halogenated compounds, anhydrides, enols, etc. which have electron affinities greater than themselves and, second, their cluster size changes with water concentration causing them to shift in drift time in the ion mobility spectrum. Similar characteristics also exist for the proton abstraction reaction. For a microprocessor controlled ion mobility spectrometer system, it is desirable to eliminate both of these problems in order to provide identification specificity.

SUMMARY OF THE INVENTION

The invention is an improvement to an ion mobility spectrometer wherein a sample gas or vapor having at least one constituent to be detected and a carrier gas are injected into the reaction chamber of the ion mobility spectrometer, the improvement characterized by the addition of at least one reagent source mixing at least one reagent with the carrier gas to enhance the specificity of the spectrometer. At least one reagent is selected to have a high proton affinity, electron affinity, or acidity while at the same time maintaining reactivity with the sample molecule. In the preferred embodiment at least one reagent is acetone for positive ions and carbon tetrachloride for negative ions. The advantage of using acetone and/or carbon tetrachloride as the reagent is that they provide identification specificity for ion mobility spectrometry. In addition, acetone provides an ion mobility peak which does not cluster with water thereby providing a single narrow fixed peak in the ion spectrum which can be used as a calibration point in algorithms of automated ion mobility spectrometer systems. Other advantages will become more apparent from reading the specification in connection with the appended figures.

BRIEF DESCRIPTION OF THE FIGURES

FIG. 4 is a diagram of the ion mobility spectrometer system embodying the invention.

DETAILED DESCRIPTION OF THE INVENTION

Figure 1:
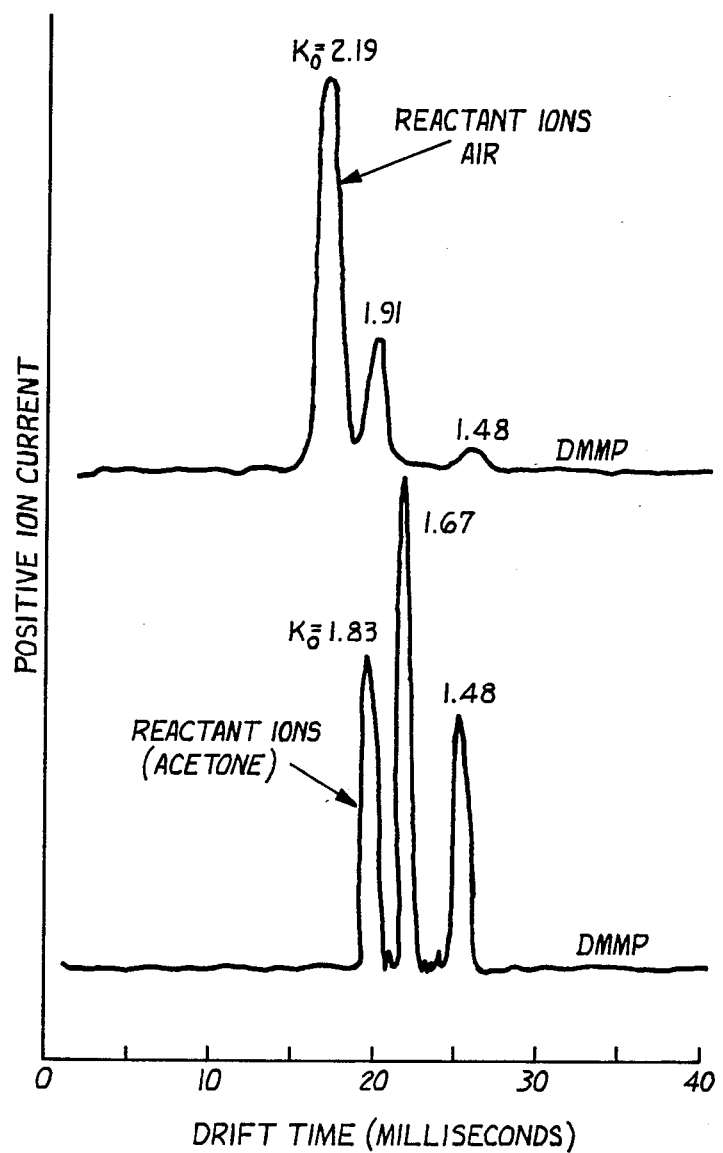
FIG. 1 is positive ion mobility spectra for DMMP using $(H_2O)_nH^+$ and acetone reactant ions.

The present invention involves the addition of at least one chemical reagent to the carrier gas of an ion mobility spectrometer to modify the reactant ions. The reagent modifies the ion-molecule reaction chemistry allowing the formation of stable ions specific to a sample under atmospheric conditions. More specifically, the invention relates to, but is not limited to, the detection of carbonyl and organophosphorous compounds using acetone as a reagent and organonitro compounds using carbon tetrachloride as a reagent.

Acetone

The response of an ion mobility spectrometer to acetone produces a single ion mobility peak with a drift time ratio $K_o$ of 1.19 relative to $(H_2O)_nH^+$ for a drift temperature of 50° C. With a mass spectrometer coupled to the ion mobility spectrometer, the ions contributing to the single ion mobility peak of acetone have been shown to be protonated acetone dimers. The proton affinity of the acetone dimer is given by:

$$P.A.[(CH_3COCH_3)_2H^+] = P.A.[(CH_3COCH_3)H^+] + \Delta H_{1,2} - \Delta H_{vap}.$$

where $P.A.[(CH_3COCH_3)H^+]$ is the proton affinity of the acetone monomer (197.2 Kcal/mole)

$\Delta H_{1,2}$ is the heat of reaction of the acetone dimer from the acetone monomer (approximately 37 Kcal/mole)

$\Delta H_{vap}$ is the heat of vaporization for acetone (7.6 Kcal/mole)

The proton affinity for the acetone dimer, $P.A.[(CH_3COCH_3)_2H^+]$, is approximately 226.6 Kcal/mole. This proton affinity exceeds that for ionized water vapor, $(H_2O)_nH^+$, by as much as 54 Kcal/mole and exceeds that for clustered ammonia vapor ions, $(H_2O)_nNH^+_4$, by as much as 22 Kcal/mole. Thus as a reactant ion in ion mobility spectrometry, the dimer of acetone provides greater specificity of response than water or ammonia vapor due to its higher proton affinity.

Further, mass spectrometric data has demonstrated that the protonated dimer ion of acetone does not cluster with water. For water concentrations up to 20 ppm (parts per million), the response to acetone was the protonated dimer while for water concentrations greater than 200 ppm in the carrier gas, no dimer ion of acetone was observed. The protonated dimer ion of acetone disappears when the proton affinity of $(H_2O)_nH^+$ and $(H_2O)_nNH^+_4$ increases due to clustering activity with water. Consequently, the acetone reactant ion must be used with carrier and drift gases having low concentrations of water. Conversely, however, when the water concentration of the carrier and drift gases is low, the position of the acetone dimer peak will not shift due to the clustering activity of water. As previously indicated, this property of acetone allows the protonated dimer peak to serve as a calibration peak for alogrithm development purposes.

Those skilled in the art will recognize that the properties of the protonated dimer of acetone should also be shared by other compounds in the same chemical class as acetone. That is, any ketone, carbonyl, sulfoxide, or phosphoryl compound may be used as a reagent in the place of acetone.

The ionization of organophosphorous compounds are dependent on the nature of the positive reactant ions in the ion mobility spectrometer. When using protonated water vapor, $(H_2O)_nH^+$, as the reactant ion, mass spectrometric data shows that the ions contributing to the various peaks of dimethylmethylphosphonate (DMMP) in FIG. 1 are $DMMP(H_2O)_nH^+$ and $DMMP_2H^+$ with reduced mobilities of 1.91 and 1.48 $cm^2V^{-1}s^{-1}$ respectively. When using the protonated dimer of acetone for a reactant ion, mass spectrometric data shows that the observed ions of dimethylmethylphosphonate are $DMMP(CH_3COCH_3)H^+$ and $DMMP_2H^+$ with reduced mobilities 1.67 and 1.48 $cm^2V^{-1}s^{-1}$ respectively. Consequently under normal operating conditions (i.e. less than 20 ppm water in the drift and carrier gases) the drift times for the two peaks from DMMP are unaffected by water clustering. Therefore narrow time windows may be used to detect the presence of and quantity of DMMP in the sample. Similar results have also been observed for other organophosphorous and carbonyl compounds.

In U.S. Pat. No. 4,259,573, Prober and Dam disclose the use of hexafluoroacetone in air to calibrate the concentration response of ion mobility spectrometry. Besides not specifying a concentration calibration technique but rather an ion modification technique, the present disclosure differs from that by Prober and Dam in that hexafluoroacetone would not be selected, as a reagent because of its low proton affinity (159.3 Kcal/mole). A reagent having a low proton affinity offers little advantage in increasing identification specificity of ion mobility spectrometry.

Carbon Tetrachloride

The response of an ion mobility spectrometer to carbon tetrachloride produces a single ion mobility peak with a drift time ratio of 0.89 relative to $(H_2O)_nCO_4^-$ for a drift temperature of 108° C. With a mass spectrometer coupled to the ion mobility spectrometer, the ions contributing to the single ion mobility peak of carbon tetrachloride have been shown to be $(H_2O)_nCl^-$ ions.

The electron affinity of chlorine is 2.32–2.45 electron volts. This electron affinity exceeds that for oxygen by as much as 2 electron volts. The acidity of chlorine (HCl) is characterized by a $\Delta H°_{acid}$ of 333.3 Kcal/mole. this acidity exceeds that for oxygen ($\Delta H°_{acid} = 350.6$ Kcal/mole) by 17.3 Kcal/mole. Thus as a reactant ion in ion mobility spectrometry, the $(H_2O)_nCl^-$ ion of carbon tetrachloride provides greater specificity of response than $(H_2O)_nCO_4^-$ or $(H_2O)_nO_2^-$ due to its higher electron affinity and greater acidity.

Those skilled in the art will recognize that the ability of carbon tetrachloride to produce $(H_2O)Cl^-$ ions is also shared by other chlorinated compounds. That is, methylene chloride, dichlorobenzene, etc. may be used as a reagent in place of carbon tetrachloride.

Figure 3:
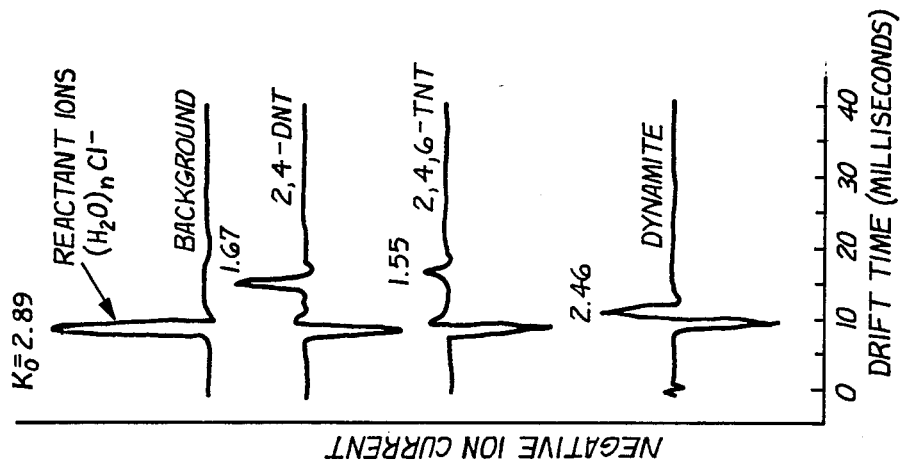
FIG. 3 is negative ion mobility spectra for various organonitro compounds using $(H_2O)_nCl^-$ reactant ions. Background is subtracted from the product ion signatures.
Figure 2:
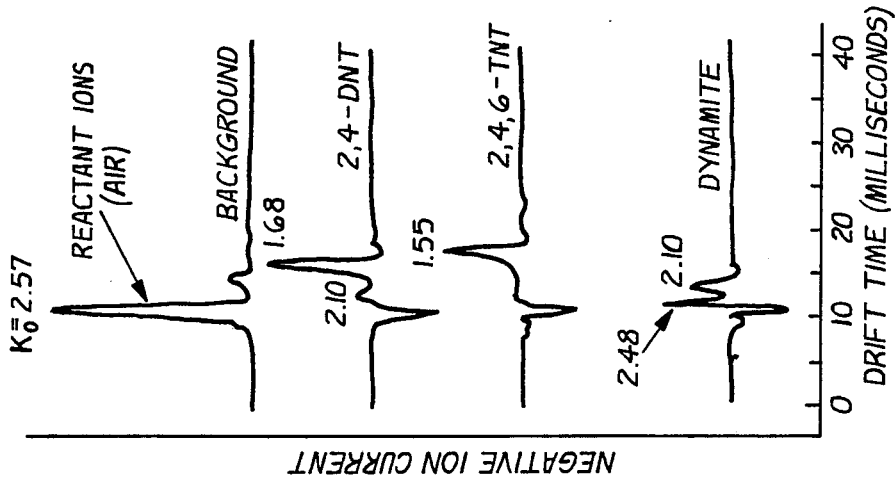
FIG. 2 is negative ion mobility spectra for various organonitro compounds using $(H_2O)_nCO_4^-$ reactant ions. Background is subtracted from the product ion signatures.

The ionization of organonitro compounds are dependent on the nature of the negative reactant ions in the ion mobility spectrometer. When using a purified water free nitrogen as the carrier gas, free electrons serve as reactant ions and the ions produced from dinitrotoluene (DNT) and trinitroluene (TNT) are the $M^-$ molecular negative ion. When using a purified air as the carrier gas, $(H_2O)_nCO_4^-$ ions serve as reactant ions and the ions produced from DNT and TNT are the proton abstracted $(M-H)^-$ negative ions. When carbon tetrachloride reagent vapors are added to either the purified nitrogen or purified air carrier gases, the $(H_2O)_nCl^-$ ions serve as reactant ions and the ions produced from DNT and TNT are the proton abstracted $(M-H)^-$ negative ions. Similar results have also been obtained from other organonitro compounds as shown FIGS. 2 and 3 for the $(H_2O)_nCO_4^-$ and $(H_2O)_nCl^-$ reactant ions respectively. A comparison of dynamite signatures shows how the $(H_2O)_nCl^-$ reactant ion eliminates responses from interfering vapors, $K_0 = 2.10$, as illustrated in FIG. 3. In addition, $(H_2O)_nCl^-$ ions can also be used to attach to a sample molecule to produce $(M+Cl)^-$ ions. Sample compounds which are alkylating agents or contain "active" hydrogens, e.g. captan, dieldrin and dimethylsulfoxide, can be detected and identified in this manner.

Those skilled in the art will recognize that other halogen ions such as $(H_2O)_nBr^-$ and $(H_2O)_nI^-$ will display chemistry similar to $(H_2O)_nCl^-$ ions. The $(H_2O)_nBr^-$ and $(H_2O)_nI^-$ ions can be produced in ion mobility spectrometry by using brominated and iodized reagent compounds such as dibromobenzene and iodobenzene respectively.

Implementation

The details of an ion mobility spectrometer embodying the concept of using protonated acetone or carbon tetrachloride to form the reactant ion is shown in FIG. 4. Referring to FIG. 4, the ion mobility spectrometer 10 is of the type disclosed in U.S. Pat. No. 4,311,699 having a reaction chamber 12, a drift chamber 14 and permeable membrane sample input 16. As is known in the art, the ion mobility spectrometer includes suitable heating means, not shown, to provide an appropriate operating temperature, and biasing means for providing potentials to the electrodes 18 disposed along the length of the ion mobility spectrometer to establish a proper electrical potential gradient from the entrance aperture 20 to a collector electrode 22.

The reaction chamber 12 and drift chamber 14 are separated by an injection grid 24 electrically connected to the output of a Pulse Generator 26. The Pulse Generator 26 generates a first electrical signal biasing injection grid at a potential inhibiting the ion flow from the reaction chamber 12 to the drift chamber 14. Periodically the Pulse Generator 26 generates a second signal in the form of a short duration pulse biasing injection grid at a potential permitting the ions to flow through injection grid 24 from the reaction chamber 12 to the drift chamber 14. The ions transmitted through injection grid 24, during the occurrence of the second signal, drift across the length of the drift chamber 14 under the influence of the electric field provided by electrodes 18, and are collected by ion collector electrode 22.

The ions collected by ion collector electrode 22 create an electrical signal which is amplified by Amplifier 28 such as an electrometer circuit. The output of Amplifier 28 is communicated to the Electronic Processing Unit (EPU) 30. The Electronic Processing Unit 30 also receives the signals generated by the Pulse Generator 26 and generates a signal characteristic of the sample as shall be explained hereinafter.

An ionizer 32 for generating the requisite ions is disposed in the reaction chamber 12 adjacent to inlet 20. Ionizer 32, may be a radioactive source, a corona discharge device, an electron source or any other such ionizing device known in the art.

The sample input 16 comprises a sample chamber 34 separated from an integral concentric mixing chamber 36 by a membrane 38. The membrane 38 is selected to selectively transmit the constituent of the sample desired to be detected and may be either a non-porous semipermeable type or a porous diffusion type as disclosed in U.S. Pat. No. 4,311,669, incorporated herein by reference. The sample chamber 34 has a sample inlet port 40 and an exhaust port 42 connected to a Sample Pump 44 by means of connecting line 46. The Sample Pump 44 provides for a continuous flow of the sample directed across the face of membrane 38.

The mixing chamber 36 comprises an inner cylindrical member 48 and an outer cylindrical member 50. The outer cylindrical member 50 supports the membrane 38 at one end and is connected to inner cylindrical member 48 by means of an annular end cap 52 at the other end. The free end of the inner cylindrical member 48 is spaced a short distance from the membrane 36 providing an internal flow path connecting the space between the internal cylindrical member 48 and external cylindrical member 50 and the interior of internal cylindrical member 48. The end of the internal cylindrical member 48 opposite membrane 38 defines the entrace aperture 20 to reaction chamber 12 opposite injection grid 24. The mixing chamber 36 has an entrance aperture 54 passing through the external cylindrical member 50 adjacent to end cap 52, receiving a mixture of the carrier gas and the reagent.

A Cell Pump 56 recirculates a carrier gas through the reaction and drift chambers 12 and 14 respectively through feed conduits 58, 60, and 62 and return conduit 64. A Filter 66 disposed at the junction of conduits 58 and 60 removes water vapor and other contaminants from the carrier gas as is known in the art. The Filter 66 may incorporate a desiccant, silica gel or be a molecular sieve. A first flow control valve 68 controls the velocity of the gas flow through the drift chamber.

Conduit 60, is also connected to Reagent Source 70. Reagent Source 70 may be a single reagent source introducing either acetone or carbon tetrachloride into the carrier gas or may be a dual Reagent Source introducing both acetone and carbon tetrachloride into the carrier gas. The Reagent Soruce 70 is connected to the mixing chamber 36 by means of conduit 72. A second flow control valve 74 controls the flow rate of the carrier gas through Reagent Source 70 and to the mixing chamber 36.

Operation

The operation of the ion mobility spectrometer is as follows: The Sample Pump causes a continuous flow of sample gas across the outer surface of membrane 38 which selectively transmits the constituent of the sample desired to be detected to the mixing chamber 36. The mixture of the reagent and carrier gases input to mixing chamber 36 from the Reagent Source 70 scrub the internal surface membrane 38 producing a mixture of the sample, reagent, and carrier gases which is received into the reaction chamber 12 through entrance aperture 20. As in conventional ion mobility spectrometry the mixture containing the sample is ionized in the reaction chamber and starts to drift towards the injection grid 24 under the influence of the generated electrostatic field. Because the proton affinity, electron affinity or acidity of the reactant ion of the reagent is greater than that of the normal contaminants of the sample, such as water and ammonia, but less than that of the constituent of the sample to be detected, the primary reaction will be between that of reactant ions of the reagent and the constituent of the sample desired to be detected. As previously discussed when the reagent is acetone, or similar compound, or carbon tetrachloride, or similar compound, the formed reactant ions, because of their higher proton affinity, electron affinity, or acidity will react primarily with the molecules of the constituent of the sample to be detected and will not react with the normal contaminants of the sample and carrier gas. Further since the reactant ions do not have a tendency to cluster as previously described, the ion peaks for the constituent desired to be detected will be fixed and sharply defined as long as the water content is maintained at a concentration level of less than 20 parts per million.

As in conventional ion mobility spectrometry, the injection grid 24 is periodically biased to transmit a short pulse of ions into the drift chamber, where they drift towards the collector electrode 22 under the influence of the electrostatic field. The electrical signal produced by the ions being collected by the collector electrode 22 is amplified by amplifier 28 to generate a signal indicative of the number of ions being collected at any given time. The Electronic Control Unit 30, samples the output of Amplifier 28 at predetermined time intervals after each injection pulse.

The Electronic Processing Unit 30 may perform any of the data analysis or manipulations as is known in the art. For example, the Electronic Processing Unit may output a graph displaying the ion spectrum of the reagent and sample, it may produce a visual display or print out identifying each constituent of the sample and their concentration. It also may produce a visual display or print out indicative of only one or more sample constituents of particular interest, or it may produce a simple audible alarm indicating that a particular constituent is present in the sample.

Because the peaks of the sample are sharply defined by the use of acetone or carbon tetrachloride as the reagents, the Electronic Processing Unit 30 may only sample the output of Amplifier 28 during one or more relatively narrow time intervals after each injection impulse, such drift times being indicative of drift velocity of the particular constituent or constituents in the sample.

Further, since the reagent does not cluster with water, the ion peak of the reactant ion itself will also be well defined. This permits the peaks of the reactant ion to be used as calibration points for the algorithms used in the Electronic Processing Unit 30. When developing the algorithm for the ion mobility spectrometer, drift time is of major importance in the signature of the detected ions. The drift time, $t_d$, is the time it takes for the ion to arive at the ion collector electrode after it has been injected into the drift chamber 14 by injector grid 24. The drift time $t_d$ is given by:

$$t_d = l_d/V_d$$

where: $l_d$ is the length of the drift chamber 14 and $V_d$ is the drift velocity of the detected ion.

The drift velocity of the detected ion is given by:

$$V_d = KE$$

where: $K$ is the ion mobility and $E$ is the gradient of the electrostatic field. In general $K$ is dependent on temperature and pressure but these parameters can be removed by defining the reduced mobility of the ion $K_o$, normalized for standard temperature ,T, and pressure ,P $$K_o = K(273/T)(P/760)$$

The equation for the drift time of the detected ion, $t_d$, can be rewritten as follows:

$$t_d = \frac{l_d}{K_o E}\left(\frac{T}{273}\right)\left(\frac{760}{P}\right)$$

If a calibration ion, i.e. one having fixed peaks, exists in the ion spectrum at all times, then the drift time of the constituents of the sample, $t_{ds}$, relative to the drift time of the calibration ion, $t_{dc}$, satisfy the relationship $$t_{ds}/t_{dc} = K_{oc}/K_{os}$$

where $K_{oc}$ is the mobility of the calibration ion and $K_{os}$ is the mobility of the sample ion. The above relationship is independent of temperature and pressure provided the chemical composition of the constituents of the sample do not change. One of the major causes of chemical change in ion mobility spectrometry is the clustering of water. The use of acetone as the reagent not only provides the desired calibration peaks but also quenches the water cluster mechanism and makes drift time ratios constant over a wider temperature and pressure range.

Figure 5:
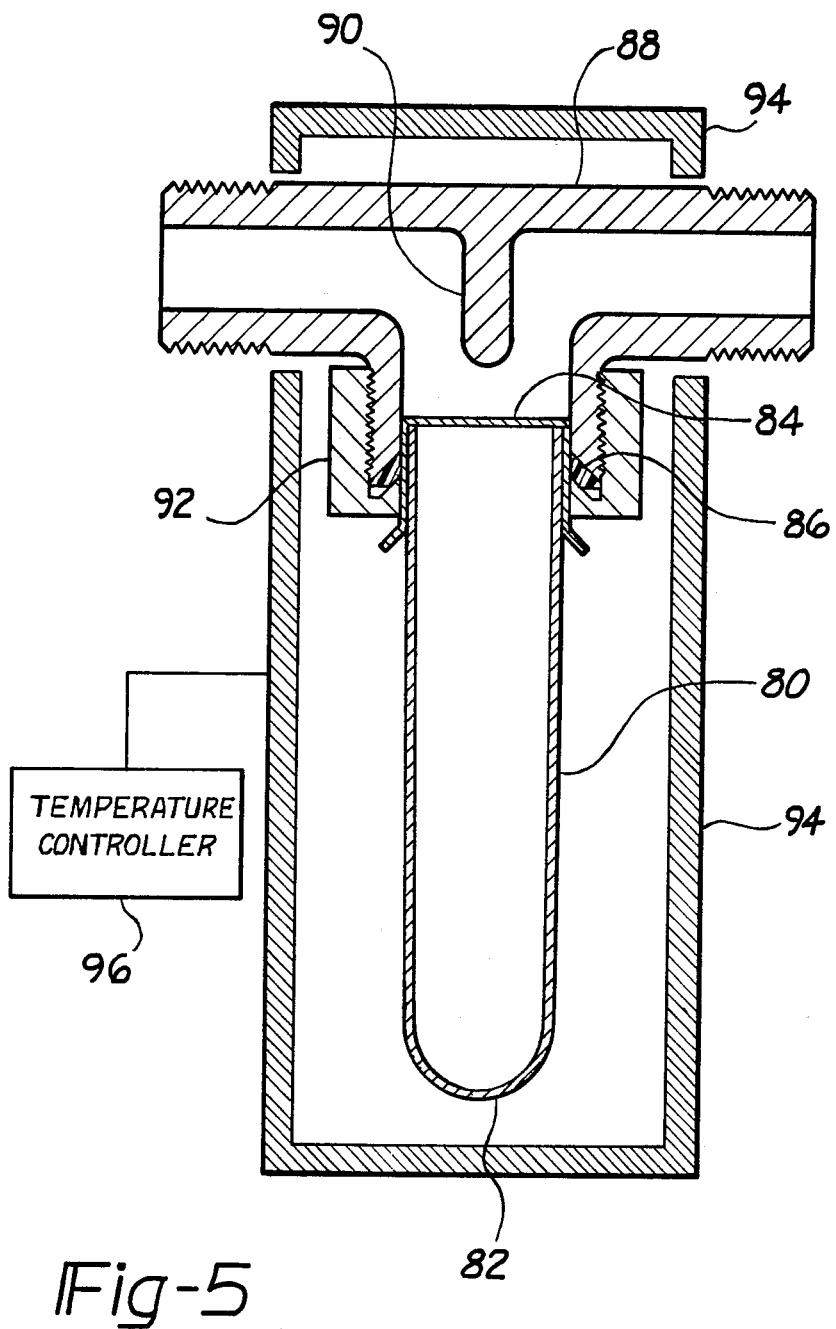
FIG. 5 is cross sectional view of the reactant source.

The details of the Reagent Source 70 for a single reagent are shown in FIG. 5. Referring to FIG. 5, the Reagent Source comprise a non-porous container or tube 80 filled with acetone or carbon tetrachloride having a closed end 82. In the preferred embodiment tube 80 is made from, but not limited to stainless steel and is about 6 millimeters (¼ inch) in diameter. The closed end 82 may be formed integral with tube 80 as shown or may be a separate cap (not shown) sealing the end of tube 80 as is known in the art.

The open end of tube 80 is covered by a permeable membrane 84 comprising, for example, three sheets of poly-propylene approximately 12 to 13 microns thick. The membrane 84 is held over the end of tube 80 by a teflon ferrule 86 which is captivated between an inwardly tapered shoulder of a "T" pipe fitting 88 and a cap nut 92. The "T" pipe fitting 88 may include a baffle 90 directing the carrier gas over the surface of membrane 84.

The permeability of the membrane 84 is such that the Reagent Sources 70 containing acetone or carbon tetrachloride as the reagent, will produce a reagent concentration of 8 parts per million in a carrier gas. This concentration is kept constant by regulating the temperature of the Reagent Source by means of a heater or heater/cooler element 94 controlled by temperature controller 96. When both acetone and carbon tetrachloride are desired to be used as reagents, either simultaneously or independently, the Reagent Source 70 will comprise two Reagent Sources such as shown on FIG. 5 with membranes 84 of both Reagent Sources exposed to the carrier gas.

Those skilled in the art will recognize that membrane 84 is not limited to polypropylene but many include other materials such as dimethylsilicone, polyethylene, polystyrene, ceran, etc. Also the tube containing the acetone and carbon tetrachloride may be a closed plastic or polymeric tube ("permeation tube") with permeable walls or a solid plastic or polymeric source impregnated with acetone and carbon tetrachloride. Permeation would be adjusted by the wall thickness of the plastic or polymeric tube or the degree of impregnation of the solid source.

We claim:

1. In an ion mobility spectrometer wherein a sample gas or vapor having at least one constituent to be detected and a carrier gas are injected into a reaction chamber thereof, and wherein the sample gas contains contaminants which reduce the specificity of the ion mobility spectrometer to the at least one constituent to be detected, an improvement characterized by:

at least one reagent source for introducing a reagent into the carrier gas prior to being injected into the ion mobility spectrometer, and a reagent having a higher proton affinity, electron affinity, or acidity than said contaminants, a lower proton affinity, electron affinity, or acidity than said at least one constituent to be detected, and which does not cluster with water disposed in said reagent source.

2. The ion mobility spectrometer of claim 1 wherein said reagent is selected from a group which includes ketones, carbonyl or phosphoryl compounds, and halogenated compounds.

3. The ion mobility spectrometer of claim 2 wherein said reagent is acetone.

4. The ion mobility spectrometer of claim 1 wherein said reagent is carbon tetrachloride.

5. The ion mobility spectrometer of claim 1 wherein said at least one reagent source is two reagent sources, one of said reagent sources having said reagent disposed therein and the other of said reagent sources having a different reagent.

6. The ion mobility spectrometer of claim 5 wherein said reagent is acetone and said different reagent is carbon tetrachloride.

7. The ion mobility spectrometer of claim 1 wherein said ion mobility spectrometer includes a membrane interface separating the sample gas from the carrier gas to reduce the quantity of contaminants in the sample from being injected into the ion mobility spectrometer.

8. The ion mobility spectrometer of claim 7 wherein said membrane interface is selectively permeable to said at least one constituent of the sample to be detected.

9. The ion mobility spectrometer of claim 1 wherein said ion mobility spectrometer has a carrier conduit for conveying said carrier gas thereto said reagent source comprises at least one nonporous container for holding said reagent, said container having at least an output aperture;

means for coupling the output aperture of said container to said carrier conduit;

a permeable membrane interposed between the reagent in said container and the carrier gas in said carrier conduit for transmitting said reagent to said carrier gas at a predetermined rate; and means for controlling the temperature of said reagent source.

10. The ion mobility spectrometer of claim 9 wherein said reagent is selected from the group including ketones, carbonyl, or phosphoryl compounds, and halogenated compounds.

11. The ion mobility spectrometer of claim 10 wherein said reagent is acetone.

12. The ion mobility spectrometer of claim 9 wherein said permeable membrane is at least one sheet of polypropylene disposed over said output aperture.

13. A method for increasing the specificity of an ion mobility spectrometer to the constituents of a sample characterized by the steps of:

continuously mixing with a carrier gas, at least one reagent having a higher proton affinity, electron affinity, or acidity than the constituents of the sample to be detected and which does not cluster with water to form a reagent/carrier mixture;

combining said reagent/carrier mixture with a sample gas to form a reagent/carrier/sample mixture; and ionizing said reagent/carrier/sample mixture to form stable ions of said reagent, said stable ions reacting with said sample to produce ions characteristic of the constituents of the sample.

14. The method of claim 13 wherein said step of ionizing said reagent/carrier/sample mixture forms stable dimer ions.

15. The method of claim 13 wherein said step of mixing mixes with said carrier gas a reagent selected from the group including ketones, carbonyl, and phosphoryl compounds.

16. The method of claim 15 wherein said step of mixing mixes acetone with the carrier gas.

17. The method of claim 13 wherein said at least one reagent comprises said at least one reagent plus a second reagent.

18. The method of claim 17 wherein said at least one reagent is acetone and said second reagent is carbon tetrachloride.

19. The method of claim 13 wherein said step of combining comprises the steps of:

flowing said sample gas over one surface of a permeable membrane interface operative to selectively transmit the constituents of the sample gas to be detected; and flowing said reagent/carrier mixture over the opposite surface of said membrane interface to combine the transmitted constituents of the gas sample with said reactant/carrier mixture to form said reactant-/carrier/sample mixture.

20. An ion mobility spectrometer system comprising:

an ion mobility spectrometer having a reaction chamber, a contiguous drift chamber, an injection grid separating said reaction and drift chambers, ionization means disposed in said reaction chamber, a collector electrode disposed in said drift chamber opposite said injection electrode and means for generating a electrostatic field gradient across said contiguous reactant and drift chambers;

pump means for supply a continuous flow of a carrier gas though said reaction and drift chambers means for injecting a sample gas having at least one constituent to be detected into the carrier gas flow supplied to said reaction chamber;

reagent source means for injecting at least one reagent into the flow of carrier gas supplied to said reaction chamber, said reagent having a proton affinity, electron affinity, or acidity greater than water an less the constituents of the sample gas to be detected and which does not cluster with water;

means for periodically generating an injection signal biasing said injection grid for a short period of time to transmit a portion of the ions generated in said reaction chamber to said drift chamber;

amplifier means for generating an ion signal indicative of the number of ions collected by the collector electrode; and an electronic processing unit responsive to the time differential between said injection signal and said ion signals for generating a signature indicative of the characteristics of the sample gas.

21. The ion mobility spectrometer system of claim 20 wherein said pump means comprises:

a pump for recirculating said carrier gas through said reaction and drift chambers, and a filter for removing at least water, ammonia, and oxides of nitrogen from said carrier gas.

22. The ion mobility spectrometer system of claim 20 wherein said pump means comprises:
a pump for recirculating said carrier gas through said reaction and drift chambers,
a filter for removing water from said recirculation carrier gas; and
means for controlling the flow rate of said carrier gas through said reaction and drift chambers.

23. The ion mobility spectrometer system of claim 20 wherein said reagent source means comprises:
at least one nonporous container having an outlet aperture, said container containing at least one reagent;
means for coupling the outlet aperture of said container to said flow of carrier gas to said reaction chamber; and
a permeable membrane interposed between said outlet aperture and said flow of carrier gas for transmitting said reagent to said carrier gas at a predetermined rate.

24. The ion mobility spectrometer system of claim 20 wherein said reagent form stable dimer ions when ionized by said means for ionizing.

25. The ion mobility spectrometer system of claim 24 wherein said reagent is acetone.

26. The ion mobility spectrometer system of claim 20 wherein said at least one reagent is two reagents and wherein one of said two reagents is acetone and the other of said two reagents is carbon tetrachloride.

27. The ion mobility spectrometer system of claim 20 wherein said means for injecting a sample gas to said flow of carrier gas comprises:
a permeable membrane operative to selectively transmit at least one constituent of the sample to be detected;
means for directing a flow of said sample over one surface of said permeable membrane;
means for directing the flow of carrier gas over the opposite surface of said permeable membrane to mix the carrier gas with the constituents of the sample permeated through said peremeable membrane; and
means for conducting the mixture of said carrier and said permeated constituents of said sample gas to said reaction chamber.

28. The ion mobility spectrometer system of claim 24 wherein said permeable membrane aids in the removal of water, ammonia and oxides of nitrogen from the sample.

29. In an ion mobility spectrometer wherein a sample having at least one constituent to be detected and a carrier gas are injected into the reaction chamber of the ion mobility spectrometer and wherein the sample contains contaminants including water which reduce the specificity of the ion mobility spectrometer, an improvement for increasing the specificity of the ion mobility spectrometer characterized by:
reagent source means for mixing with the carrier/gas at least one reagent having a proton affinity greater than water and less than the proton affinity of the constituents of the sample to be detected and which does not cluster with water to produce a reagent/carrier mixture;
a permeable mebrane selectively permeable to the at least one constituent of the sample to be detected;
means for directing a flow of the sample onto one surface of said permeable membrane;
means for directing a flow of said reagent/carrier mixture onto the opposite surface of said permeable membrane to mix said reagent and carrier gas with the constituents of the sample permeated therethrough; and
means for conducting said reagent/carrier mixture and the permeated constituents of the sample into the reaction chamber of said ion mobility spectrometer.

30. The ion mobility spectrometer of claim 29 wherein said reagent forms stable dimer ions.

31. The ion mobility spectrometer of claim 29 wherein said reagent is selected from the group including ketones, and carbonyl or phosphoryl compounds.

32. The ion mobility spectrometer of claims 30 or 31 wherein said reagent is acetone.

33. The ion mobility spectrometer of claim 29 wherein said source means mixes said at least one reagent and a second reagent with said carrier gas.

34. The ion mobility spectrometer of claim 33 where said at least one reagent is acetone and said second reagent is carbon tetrachloride.

* * * * *